United States Patent [19]

Sharpe et al.

[11] Patent Number: 5,484,788
[45] Date of Patent: Jan. 16, 1996

[54] BUSPIRONE AS A SYSTEMIC IMMUNOSUPPRESSANT

[75] Inventors: Richard J. Sharpe, Gloucester; Kenneth A. Arndt, Newton Centre; Stephen L. Galli, Winchester; Peter C. Meltzer, Lexington; Raj K. Razdan, Belmont; Howard P. Sard, Arlington, all of Mass.

[73] Assignee: Beth Israel Hospital Association, Boston, Mass.

[21] Appl. No.: 37,271

[22] Filed: Mar. 26, 1993

[51] Int. Cl.$^6$ .................................. A61K 31/505
[52] U.S. Cl. ........................................... 514/275
[58] Field of Search .......................... 544/324; 514/275

[56] References Cited

U.S. PATENT DOCUMENTS

| | | | |
|---|---|---|---|
| 3,717,634 | 2/1973 | Wu et al. | 260/256.4 |
| 3,976,776 | 8/1976 | Wu et al. | 424/251 |
| 4,182,763 | 1/1980 | Casten et al. | 424/251 |
| 4,351,939 | 9/1982 | Simms et al. | 544/230 |
| 4,417,049 | 11/1983 | Sims | 544/231 |
| 4,438,119 | 3/1984 | Allen et al. | 424/251 |
| 4,468,391 | 8/1984 | Voith | 424/244 |
| 4,515,947 | 5/1985 | Sandefur et al. | 544/295 |
| 4,620,006 | 10/1986 | Sandefur et al. | 544/402 |
| 4,634,703 | 1/1987 | Kurtz et al. | 514/252 |
| 4,636,563 | 1/1987 | Abou-Gharbia | 546/87 |
| 4,640,921 | 2/1987 | Othmer et al. | 514/252 |
| 4,687,772 | 8/1987 | Alderdice | 514/273 |
| 4,696,927 | 9/1987 | Gittos et al. | 514/236 |
| 4,709,027 | 11/1987 | Abou-Gharbia et al. | 544/6 |
| 4,732,984 | 3/1988 | Abou-Gharbia et al. | 544/295 |
| 4,748,240 | 5/1988 | Stack et al. | 544/47 |
| 4,777,173 | 10/1988 | Shrotryia et al. | 514/252 |
| 4,788,189 | 11/1988 | Glazer | 514/221 |
| 4,810,789 | 3/1989 | Behme et al. | 544/230 |
| 4,812,567 | 3/1989 | Abou-Gharbia | 544/230 |
| 4,851,533 | 7/1989 | Abou-Gharbia | 544/405 |
| 4,883,875 | 11/1989 | Abou-Gharbia | 546/16 |
| 4,895,848 | 1/1990 | Traber et al. | 514/255 |
| 4,900,835 | 2/1990 | Abou-Gharbia | 546/272 |
| 4,927,934 | 5/1990 | Abou-Gharbia et al. | 546/152 |
| 4,940,585 | 7/1990 | Hapworth et al. | 424/464 |
| 4,943,428 | 7/1990 | Lucot et al. | 424/10 |
| 4,963,557 | 10/1990 | Badger et al. | 514/278 |
| 5,015,646 | 5/1991 | Simms | 514/253 |
| 5,032,578 | 7/1991 | Horovitz | 514/19 |
| 5,053,508 | 10/1991 | Schiehser et al. | 544/357 |
| 5,096,908 | 5/1992 | Gidda et al. | 514/307 |
| 5,098,889 | 3/1992 | Costall et al. | 514/19 |
| 5,114,947 | 5/1992 | Imondi | 514/282 |
| 5,134,140 | 7/1992 | Stack | 514/212 |
| 5,162,322 | 11/1992 | Taylor, Jr. et al. | 514/252 |
| 5,167,616 | 12/1992 | Haak et al. | 604/20 |
| 5,169,638 | 12/1992 | Dennis et al. | 424/457 |
| 5,183,819 | 2/1993 | Abou-Gharbia et al. | 514/255 |
| 5,185,329 | 2/1993 | Gawin et al. | 514/159 |
| 5,187,277 | 2/1993 | Komissarov et al. | 544/362 |
| 5,244,902 | 9/1993 | Sharpe et al. | 514/278 |
| 5,290,783 | 3/1994 | Sharpe et al. | 514/278 |

FOREIGN PATENT DOCUMENTS

| | | |
|---|---|---|
| 170213 | 7/1985 | European Pat. Off. . |
| 223344 | 9/1986 | European Pat. Off. . |
| 440851 | 2/1990 | European Pat. Off. . |
| 442423 | 2/1991 | European Pat. Off. . |
| 497314 | 8/1992 | European Pat. Off. . |
| 2654934 | 5/1991 | France . |
| 2089341 | 6/1982 | United Kingdom . |
| 2139217 | 11/1984 | United Kingdom . |
| WO88/07529 | 10/1988 | WIPO . |
| WO92/00070 | 1/1989 | WIPO . |
| WO89/03676 | 5/1989 | WIPO . |
| WO89/04311 | 5/1989 | WIPO . |
| WO91/02527 | 3/1991 | WIPO . |
| WO91/02497 | 3/1991 | WIPO . |
| WO91/13622 | 9/1991 | WIPO . |
| WO92/09252 | 6/1992 | WIPO . |
| WO92/19226 | 11/1992 | WIPO . |
| WO93/04681 | 3/1993 | WIPO . |
| WO93/12789 | 7/1993 | WIPO . |

OTHER PUBLICATIONS

Allen, L. E., et al., *Arneimittel-Forsch*, vol. 24, p. 917 (1974).

Ameisen, J. C., et al., "A New Interpretation of the involvement of Serotonin in Delayed–Type Hypersensitivity," *J. Immunology*, vol. 142, No. 9, pp. 3171–3179 (1989).

Arndt, K. A., et al., "The Pharmacology of Topical Therapy," *Dermatology in General Medicine*, Ch. 211, 2532–40, T. B. Fitzpatrick, A. Z. Eisen, K. Wolff, I. M. 1988.

Caccia, S., et al., "Disposition and metabolism of buspirone and its metabolite 1–(2–pyrimidinyl)–piperazine in the rat," *Xenobiotica* 13 (3):147–153 (1983).

Blozovski and Sivadjian, "The Action of Serotonin, Reserpine and Other Pharmacological Agents on Sudoral Secretion", *Chemical Abstracts*, vol. 54, 21504 (1960).

Dostal, G. and Gamelli, R. L., "The Differential Effect of Corticosteroids on Wound Disruption Strength in Mice," *Arch. Surg.*, vol. 125, pp. 636–640 (1990).

Eison, A. S., Temple, D. L., "Buspirone: Review of its Pharmacology and Current Perspectives on its Mechanism of Action," *Am. J. Med.*, vol. 80, pp. 1–51 (1986).

Freire-Garabal, M., et al., "Effects of Buspirone on the Immunosuppressive Response to Stress in Mice," *Arch. Int. Pharmacodyn.*, 314, 160–168 (1991).

Fishel, R., et al., "Cyclosporin A Impairs Wound Healing In Rats," *J. Surg. Research*, vol. 34, pp. 572–575 (1983).

Galli and Hammel, "Unequivocal Delayed Hypersensitivity in Mast Cell–Deficient and Beige Mice", *Science*, vol. 226, 710–13 (1984).

(List continued on next page.)

*Primary Examiner*—Marianne M. Cintins
*Assistant Examiner*—Phyllis G. Spivack
*Attorney, Agent, or Firm*—Cheryl K. Zalesky; Kilpatrick & Cody

[57] ABSTRACT

A method for suppressing an immune response in a mammal by systemically treating the mammal with an effective amount of buspirone that is capable of inhibiting classic contact hypersensitivity reactions.

10 Claims, 4 Drawing Sheets

OTHER PUBLICATIONS

Goa, K. L., and Ward, A., "Buspirone: A Preliminary Review of Its Pharmacological Properties and Therapeutic Efficacy as an Anxiolytic," *Drugs,* vol. 32, pp. 114–129 (1986).

Goldberg, L., and Finnerty, R., "Comparative Efficacy of Buspirone and Diazepam in the Treatment of Anxiety," *Am. J. Psychiatry,* vol. 136, No. 9, pp. 1184–1187 (1979).

Hellstrand, K., and Hermodsson, M. S., "Role of Serotonin in the Cell Regulation of Human Natural Killer Cell Cytotoxicity," *J. Immunology,* vol. 139, No. 3 pp. 869–875 (1987).

Jann, M. W., "Buspirone: An Update on a Unique Anziolytic Agent," Pharmacotherapy, vol. 8, No. 1, pp. 100–116 (1988).

Jun, D. D., et al., *J. Invest. Dermatol.,* vol. 90, p. 311 (1988).

Kligman, A. M., "The Comparative Histopathology of Male-Pattern Baldness and Senescent Baldness," *Clinics in Dermatology,* vol. 6, No. 4, pp. 108–118 (1988).

Metys, J., et al., "Inhibition of Passive cutaneous Anaphalaxis By Several Histamine ($H_1$) and Serotonin Antagonists in the Rat," Agents and Actions, vol. 23, pp. 331–333 (1988).

Milburn, C. M., and Peroutka, S. J., *J. Neurochem.,* vol. 52, pp. 1787–1792 (1989).

New, J. S., et al., "Buspirone Analogues, 2, Structure–Activity Relationships of Aromatic Imide Derivatives," *J. Med. Chem.,* vol. 29, pp. 1476–1482 (1986).

Schroeder and Christophers, "Transient Absence of C5a–Specific Neutrophil Function in Inflammatory Disorders of the Skin", *The Journal of investigative Dermatology,* vol. 85, 194–98 (1985).

Seppala, T., et al., "Effects of Alcohol on Buspirone and Lorazepam Actions," *Clin. Pharmacol. Ther.,* pp. 201–207 (1982).

Singh, G., Corticosteroids in Corneal Endothelial Wound Healing, Annals of Opthalmology, vol. 17, No. 1 (1985).

Taylor, D. P., "Buspirone, a New Approach to the Treatment of Anxiety," *Faseb. J.,* vol. 2, pp. 2445–2452 (1988).

Tucker, "Inflammation in Acne Vulgaris: Leukocyte Attraction and Cytotoxicity by Comedonal Material", *The Journal of Investigative Dermatology,* vol. 74, 21–25 (1980).

vanWauwe, P., and Goossens, J. G., "Arabinogalactan–and Dextran–induced Ear Inflammation in Mice: Differential Inhibition by H1–antihisamines, 5–HT–Serotonin Antagonists and Lipoxygenase Blockers," *Agents and Actions, vol. 28, pp. 78–82 (1989).*

Wershil et al, "Mast Cell–Dependent Amplification of an Immunologically Nonspecific Inflammatory Response", *Journal of Immunology,* vol. 140, 2356–60 (1988).

Wong, D. T. W., et al., "Human Eosinophils Express Transforming Growth Factor–Alpha," *J. Exp. Chem.,* vol. 172, pp. 673–681 (1990).

Wong, D. T. W., et al., "Eosinophils From Patients with Blood Eosinophilia Express Transforming Growth Factor $\beta1$," *Blood,* vol. 78, pp. 2702–2707 (1991).

Wu, et al., J. Med. Chem., vol. 15, p. 477 (1972).

BUSPIRONE AS A SYSTEMIC IMMUNOSUPPRESSANT

BACKGROUND OF THE INVENTION

This invention is in the field of the suppression of immune responses, and in particular relates to a method for the treatment of immune disorders that preferably includes administering a buspirone derivative that does not have significant neuroleptic effects or is administered in a way to minimize its neuroleptic effects.

The immune system specifically recognizes and selectively eliminates foreign invaders, or other antigenic agents, by a process known as the immune response. The immune response has three major characteristics: it responds adaptively to foreign invaders, it exhibits strong specificity, and it displays a long-term memory of earlier contacts with specific foreign pathogens or antigens. The immune response involves the production of antibodies and/or the destruction of antigenic cells by T lymphocytes; both the antibodies and the T lymphocytes are highly specific for the antigenic agent.

Cutaneous contact hypersensitivity responses are complex expressions of cellular immunity characterized by antigen-dependent changes in lymphocyte traffic, the recruitment of circulating leukocytes to the site of antigen challenge (leukocyte infiltration), and alterations in vascular permeability and blood flow. While T cells are required for the expression and immunological specificity of the response, many other cell types also have roles in the reaction, including Langerhans' cells, keratinocytes, and vascular endothelial cells. Antigen presentation is thought to be effected primarily by Langerhans' cells, whereas much of the local expression of the response is thought to be regulated by cytokines derived from both T cells and accessory cells.

Pharmacological studies have indicated that a number of mediators in addition to cytokines may contribute to the expression of contact hypersensitivity and other forms of cell-mediated immunity. There has been particular interest in the role of serotonin (5-hydroxytryptamine, 5-HT) in these reactions. For example, serotonin has been shown to have a wide range of actions on T cells and other effector cells in vitro or in vivo, and pharmacological agents that deplete or antagonize serotonin can diminish expression of cell-mediated immunity. Early studies raised the possibility that such agents might reduce cell-mediated immunity by antagonizing or depleting mast cell-associated serotonin. However, more recent findings indicate that at least one of these drugs, reserpine, can inhibit contact hypersensitivity independently of mast cells, probably through direct effects on T cells.

Although experimental contact hypersensitivity represents a classical example of an immune response, and is the experimental model for the common clinical disorder, contact dermatitis, many other pathological conditions in mammals are solely or in part the result of immune responses. Examples of other pathological or undesired immune responses include host rejection of foreign organ or tissue transplants; graft-vs-host disease in which donor immunological cells present in the graft attack host tissues in the recipient of the graft; diseases with proven or possible autoimmune components, such as rheumatoid arthritis, juvenile rheumatoid arthritis, psoriatic arthritis, psoriasis, leprosy reversal reactions, erythema nodosum leprosum, autoimmune uveitis, multiple sclerosis, allergic encephalomyelitis, systemic lupus erythematosis, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, Stevens-Johnson syndrome, idiopathic sprue, Crohn's disease, ulcerative colitis, Graves ophthalmopathy, sarcoidosis, primary biliary cirrhosis, primary juvenile diabetes, uveitis posterior, and interstitial lung fibrosis; allergic asthma; and inappropriate allergic responses to environmental stimuli such as atopic dermatitis and hypersensitivity to pollen, insect stings and certain foods.

Various therapeutics have been utilized as immunosuppressants including steroid hormones, anti-metabolites such as methotrexate and azathioprine, cyclosporine, alkylating agents such as cyclophosamide and busulfan, and antibiotics. However, such agents are not always effective and/or may produce undesirable side effects. As a result, there still remains a strong need to provide new immunosuppressive agents that can minimize or prevent pathogenic immune responses.

In contrast to the immune response, an inflammatory response is a pathologic condition that can occur in response to immunologically non-specific injury, either from physical (such as trauma), chemical, or biologic agents. An inflammatory response is characterized by increased blood flow and redness in the inflamed area, increased capillary permeability and edema, and recruitment of immunologically non-specific white blood cells, especially neutrophils, that remove injurious material and/or promote repair. Unlike immune responses, inflammatory responses do not respond adaptively to the inciting stimulus, do not show specificity and do not exhibit long term memory.

Cellular products of lymphocytes may contribute to or induce an inflammatory response. However, because of the differences in mechanisms, a compound can function as an antiinflammatory agent without having immunosuppressive properties. Phenylbutazone, indomethacin, aspirin, ibuprofen, and acetaminophen are examples of antiinflammatory compounds which have no significant immunosuppressive activity, as demonstrated by their lack of a significant effect on immunologically mediated responses, such as contact hypersensitivity.

Buspirone (8-[4-[4-(2-pyrimidinyl)-1-piperaziny]butyl]-8-azaspiro[4,5]decane-7,9-dione) is a neuroleptic agent with central nervous system (CNS) dopamine and serotonin (5-HT) receptor antagonist properties.

PCT International Publication No. WO 91/02527 discloses a method and composition to treat cutaneous, mucosal, or ocular hypersensitivity that includes administering an effective amount of reserpine, spiperone, or other serotonin antagonist.

There remains a need for additional compounds that are immunosuppressants but do not exhibit significant neuroleptic activity.

It is therefore an object of the present invention to provide a method and compositions for suppressing pathogenic immune responses.

It is another object of the present invention to provide a method and compositions for suppressing pathogenic immune responses that are without significant neuroleptic effect.

SUMMARY OF THE INVENTION

A method for the treatment of a human or other mammal in need of immunosuppression is disclosed wherein the mammal is treated with an effective amount of a buspirone derivative that does not have a significant neuroleptic effect, in a pharmaceutically-acceptable diluent or carrier for systemic or topical application.

Although the parent buspirone has a strong neuroleptic effect when administered systemically (but not when administered topically), it is used in the examples as a model of an active immunosuppressant. Derivatives of buspirone which lack neuroleptic activity can be measured against this model, and are considered to be immunosuppressants if they suppress the ear swelling associated with an experimental contact hypersensitivity response by at least 40% at 24 hours after specific antigen challenge.

In the preferred method of administration, the buspirone derivatives are administered systemically, for example, by injection, in a pharmaceutical carrier such as saline, in an amount effective to immunosuppress the patient. In a second embodiment, the derivatives are administered topically in a suitable carrier to immunosuppress the patient effectively at the site of application without producing a significant neuroleptic effect. Other pharmaceutical compositions include a buspirone derivative combined with a cycloamylose, such as cyclodextrin, which can used to modify the pharmokinetics of the compound. In a preferred embodiment, buspirone or its derivative is administered as a quaternary salt.

DETAILED DESCRIPTION OF THE INVENTION

Definitions

Figure 1:
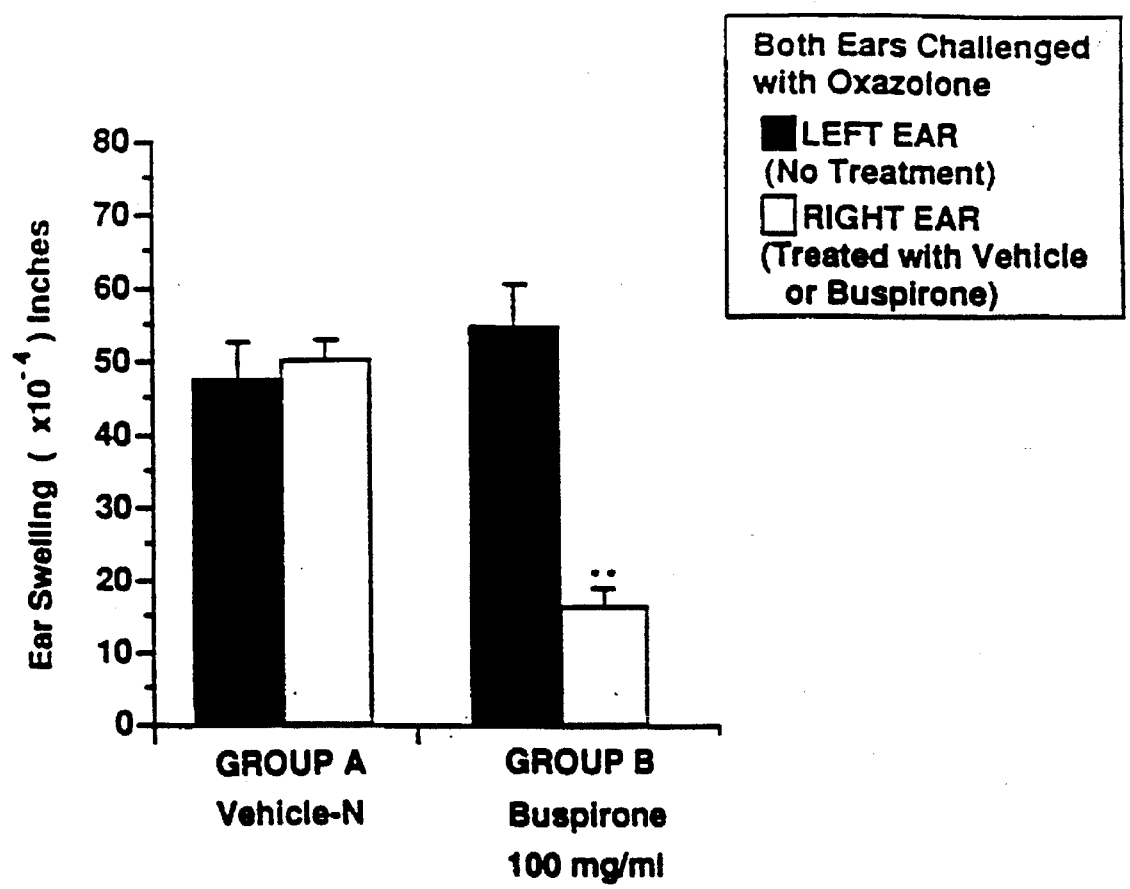
FIGS. 1 and 1a show comparative effects of mianserin HCl (Group A), trazadone HCl (Group B), haloperidol (Group C), buspirone HCl (Group D), and vehicle (Group E) (all agents administered at 50 mg/kg subcutaneously) on the tissue swelling associated with oxazolone-induced cutaneous contact hypersensitivity reactions. Buspirone, the other agents, or vehicle alone were administered to BALB/c mice 1 hour after right ears only were challenge for contact hypersensitivity. The change in ear thickness (post-challenged value minus baseline pre-challenge value) was measured 24 hours after oxazolone challenge. The data are presented as the mean±SEM. The reduction in ear swelling observed with buspirone was significant when compared to the reactions observed in the challenged right ears of the control, vehicle (Group E, olive oil) treated animals (**=p<0.01), whereas haloperidol, trazadone and mianserin did not significantly suppress the tissue swelling associated with contact hypersensitivity.
Figure 1A:
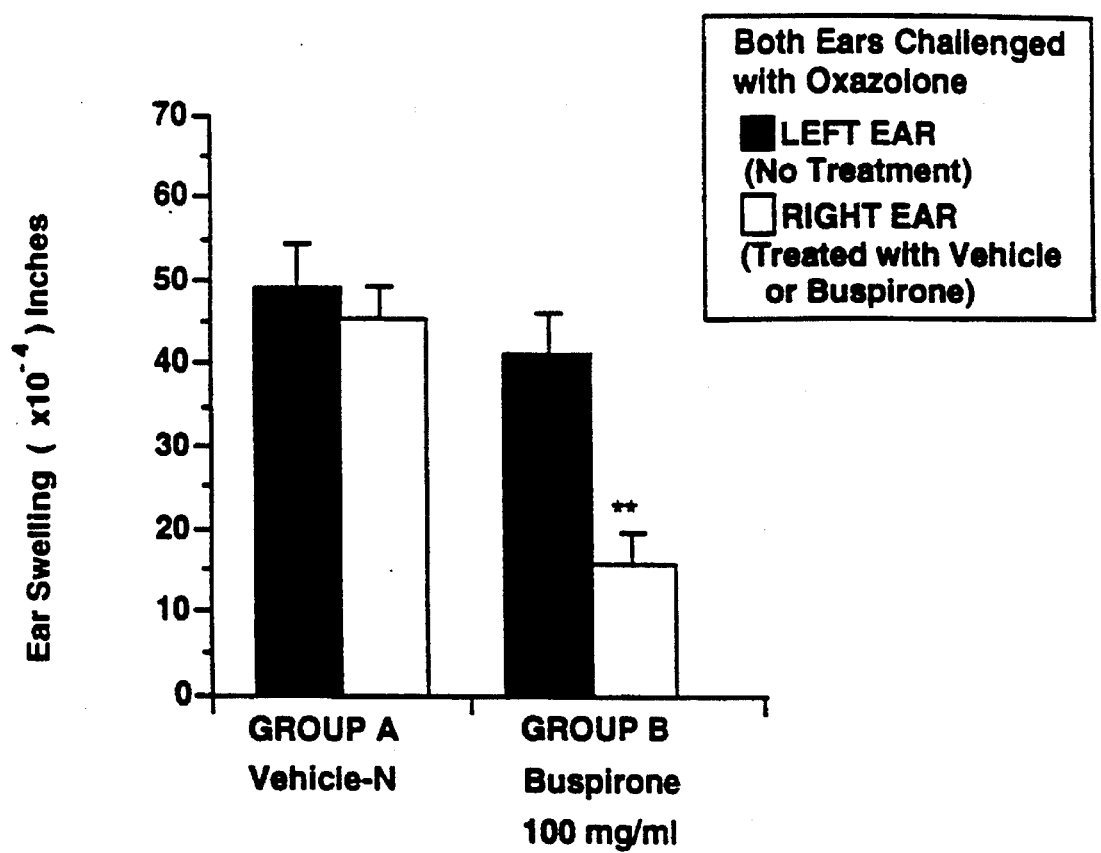

The term alkyl, as used herein, unless otherwise specified, refers to a saturated straight, branched, or cyclic hydrocarbon of $C_1$ to $C_{20}$, including methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term aryl, as used herein, and unless otherwise specified, refers to phenyl or substituted phenyl, wherein the substituent is independently halo, alkyl, or oxy(alkyl) (for example, methyoxy, ethoxy, etc.), and wherein the aryl can have up to three substituents.

The term heterocycle refers to a cyclic moiety that has O, S, or N in the aromatic ring, including but not limited to, pyrryl, furyl, pyridyl, thiophenyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, and isoxazolyl and the like, optionally substituted with halo (Cl, Br, I, or F), alkyl, oxyalkyl, aryl or oxyaryl.

The term aralkyl refers to an aryl group with an alkyl substituent.

The term alkaryl refers to an alkyl group that has an aryl substituent.

The term alkene, as referred to herein, and unless otherwise specified, refers to an alkene group of $C_2$ to $C_{10}$, and specifically includes vinyl, and allyl.

Buspirone derivatives

As used herein, buspirone derivatives without significant neuroleptic effect are identified by their ability to inhibit or prevent cutaneous contact hypersensitivity, as described in detail in Example 1. Other methods can also be used to identify these compounds, including animal models of allograft rejection, experimental allergic encephalomyelitis, lupus erythematosus, Freund's adjuvant arthritis and/or graft versus host disease. Measurement of a compound's ability to bind to serotonin or dopamine receptors can be evaluated by assessing its lack of ability to act as a tranquilizer or neuroleptic in mammals, for example, by demonstrating that it is no different than placebo, for example, in the hot plate test of Eddy, et al., *J. Pharmacol.* 107:385 (1953) and 110:135 (1954).

The chemically unrelated serotonin receptor antagonists, trazadone and mianserin, and the dopamine receptor antagonist, haloperidol, are not effective in suppressing contact hypersensitivity. On this basis, it appears that the mechanism of action of buspirone and buspirone derivatives in suppressing the immune response is independent of their serotonin or dopamine receptor blocking properties. Therefore, buspirone derivatives with immunosuppressive effects yet without neuroleptic effects can be provided by the method of selection disclosed generally herein.

As used herein, the term "buspirone derivative" refers to (1) a molecule of the formula:

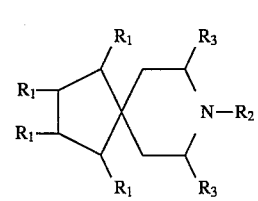

wherein:

$R_1$=H; halo (chloro, bromo, fluoro, or iodo); alkyl, specifically including $CH_3$—, cyclohexyl, $(CH_3)_2CH$—, $CH_3(CH_2)_3$—, $(CH_3)_2CHCH_2$—, $CH_3CH_2CH(CH_3)$—, $(CH_3)_3C$—, and —$CH_3(CH_2)_p$; Y—$CH_2(CH_2)_n$—; oxyalkyl; or aryl, specifically including $C_6H_5$—, (2, 3, or 4)—$(OCH_3)C_6H_4$— and (2, 3, or 4)— $(CH_3)C_6H_4$—; 2—X—$C_6H_4$—, 3—X—$C_6H_4$—, or 4—X—$C_6H_4$—; oxyaryl; or alkaryl; H, $C_6H_5CH(CH_2CH_3)CH_2$—, $C_6H_5CH(CH_3)(CH_2)_2$—, $C_6H_5CH_2CH(CH_3)CH_2$—, $C_6H_5CH_2CH_2CH(CH_3)$—, $C_6H_5CH(CH_3)(CH_2)_3$—, (2, 3, or 4)-(alkyl)—$C_6H_4CH(CH_3)(CH_2)_3$—, (2, 3, or 4)-(alkyloxy)—$C_6H_4CH(CH_3)(CH_2)_3$, (2, 3, or 4)—X—$C_6H_4$-alkyl, specifically including (2, 3, or 4)—X—$C_6H_4CH(CH_2CH_3)CH_2$—, (2, 3, or 4)—X—$C_6H_4CH(CH_3)(CH_2)$— 4—X—$C_6H_4CH(CH_3)(CH_2)_2$—, and 4—X—$C_6H_4$—$CH(CH_3)(CH_2)_3$—; $C_6H_5CH(OCH_3)(CH_2)_2$—,

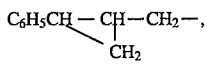

$C_6H_5CO(CH_2)_3$—, $C_6H_5CO(CH_2)_4$—, (2, 3, or 4)-(alkyl)—$C_6H_4CO(CH_2)_3$—, (2, 3, or 4)-(alkyl-oxy)—$C_6H_4CO(CH_2)_3$—, (2, 3, or 4)—X—$C_6H_4CO(CH_2)_n$—, 2-thienyl—CO—$(CH_2)_3$—, -alkyl-piperazinyl-aryl; -alkyl—$C_{3-8}$cycloalkyl-aryl; -alkyl-piperazinyl-heterocycle; -alkyl-$C_{3-8}$cycloalkyl-heterocycle; -alkyl-$C_{3-8}$cycloalkyl-$Ar_1$; -alkyl-piperazinyl-$Ar_1$; -alkenyl-piperazinyl-aryl; -alkenyl-$C_{3-8}$cycloalkyl-aryl; -alkyl-aryl-heterocycle; -alkyl-heterocycle-aryl; -alkenyl-$C_{3-8}$cycloalkyl-$Ar_1$; -alkenyl-piperazinyl-heterocycle; -alkenyl-$C_{3-8}$cycloalkyl-heterocycle; -alkenyl-piperazinyl-$Ar_1$;

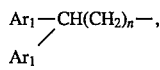

(2, 3, or 4)—X—$C_6H_4C(CH_3)CH(CH_2)_2$—, where the conformation about the double bond is cis or trans, (2, 3, or 4)—X—$C_6H_4C(CH_3)CHCH_2$—, where the conformation about the double bond is cis or trans, (2, 3, or 4)—X—$C_6H_4COCH$=$CHCH_2$—, Y—$CH_2(CH_2)_n$—, $Ar_1$—$(CH_2)_n$—, $C_1$ to $C_{20}$ alkyl, X—$(CH_2)_nCO$—, or X—$(CH_2)_n$—;

$R_3$=O, =NH, =S, chloro, bromo, iodo, fluoro, alkyl, or aryl;

n=1 to 6;

p=1 to 20;

X=is independently F, Cl, Br, I, $OCH_3$, $SO_3^-$, $NH_2$, H, —OH, —COOH, —COOR, —$SO_3$, H, —CN, —$NHSO_3H$, —$NO_2$, or —$SO_2NH$;

Y=H, F, Cl, Br, I, —$SO_3$, —$PO_4^=$, —OH, —SH, —$SCH_3$, —$CH_3SO_2^-$, —$NH_2$, or —$CO_2^-$; and $Ar_1$=independently, aryl, (2, 3, or 4—X—$C_6H_4$—, (2, 3, or 4)—$(CH_2X)C_6H_4$—, (2, 3, or 4)—$(CX_3)C_6H_4$—, (2, 3, or 4)—$(CHX_2)C_6H_4$—, 2-thienyl, or (2, 3, or 4)—X—$C_6H_4$ $CH_2$—;

or its pharmaceutically acceptable salt, including any quaternary salt known by those in the art, and specifically including the quaternary ammonium salt of the formula —$NR^+Z^-$, wherein R is alkyl (and in particular methyl or ethyl) or benzyl, and Z is a counteranion, including chloride, bromide, iodide, —O—alkyl, toluenesulfonate, methylsulfonate, sulfonate, sulfate, phosphate, or carboxylate (such as benzoate, succinate, acetate, glycolate, propionate, maleate, malate, citrate, tartrate, ascorbate, benzoate, cinnamoate, mandeloate, benzyloate, and diphenylacetate);

(2) does not have significant neuroleptic effect; and (3) exhibits an immunosuppressive effect when provided systemically or topically, as measured using the assay set out in Example 1, or as evaluated in vivo in humans by the agent's ability to inhibit contact hypersensitivity responses to patch test allergens in patients hypersensitive to a given allergen.

I. Structure and Synthesis of Buspirone Derivatives

The parent buspirone is 8-[4-[4-(2-pyrimidinyl)-1-piperaziny] butyl]-8-azaspiro[4.5]decane-7,9-dione, which has the structure illustrated below.

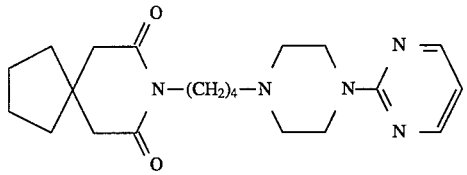

As demonstrated in Example 1, the parent buspirone has significant immunosuppressive activity. However, uncomplexed or unmodified buspirone also has significant neuroleptic effect when administered systemically. However, buspirone can be complexed, or chemically modified without undue experimentation using methods known to those skilled in the art, to retain its immunosuppressive activity and eliminate the undesired neuroleptic effect by decreasing the ability of the compound to bind to dopamine or serotonin receptors.

The potential utility of any one of the above-described forms of buspirone to act as an immunosuppressant can be conveniently determined by synthesizing the compound and testing it in the biological assay described in Example 1. The neuroleptic activity of the buspirone derivatives can be estimated as described in Example 3.

Methods of synthesis of buspirone or its derivatives are disclosed in, or can be easily adapted by one of ordinary skill in organic synthesis, from procedures disclosed in Wu, et al., *J. Med. Chem.* 15, 477 (1972), Ger. Patent No. 2,057,845, and U.S. Pat. No. 3,717,634. See also J. Clin. Psychiat. 43, 1–116 (1982).

II. Complexation or Modification of the Buspirone Nucleus to Prevent Significant Neuroleptic Effect As discussed above, immunosuppressive compounds with a buspirone nucleus that have a neuroleptic effect can be complexed or modified to eliminate that effect, by one or more of the following processes.

A. Decreasing the Lipophilicity, Equivalent to Increasing the Hydrophilicity of the Compound Compounds with a buspirone nucleus that exhibit an immunosuppressive effect yet also exhibit a neuroleptic effect can be modified to minimize the neuroleptic effect by decreasing the lipophilicity (equivalent to increasing the hydrophilicity) of the molecule. This can be done by adding one or more charged side chain(s) onto the molecule or by altering the existing side chain to make it more polar. The hydrophilicity of buspirone derivatives will in general increase when charged substituents are added.

B. Increasing the Size of the Molecule

Another technique for reducing the central nervous system (CNS) effects of compounds that contains a buspirone nucleus is to increase the size of the molecule via a covalent linkage to a large moiety (e.g., albumin or polyethylene glycol), using standard techniques of organic synthesis or by choosing a buspirone derivative with large substituents.

C. Complexing the Buspirone Nucleus with a Cyclic Molecule

A fourth method for reducing the central nervous system (CNS) effects of a compound that contains a buspirone nucleus includes forming a non-covalent complex of the compound with a cyclic molecule such as a cycloamylose (e.g., a cyclodextrin such as β-cyclodextrin), which has a spatial arrangement of hydroxyl groups whereby the outer surface of the ring formed by the cycloamylose is hydrophilic and the inner surface is lipophilic. When utilized in aqueous solution, this structure permits molecules (or parts thereof), termed "guest molecules", which are less polar than water and which are of suitable dimensions, to be incorporated into the lipophilic inner cavity, such that the cycloamylose/guest molecule complex presents to the blood-brain barrier as a relatively large and polar compound which is unable to penetrate the barrier. Such complexes may be prepared by any method known to the art, including those described in U.S. Pat. No. 4,555,504, which discloses β-cyclodextrin complexed with digoxin.

Buspirone altered or complexed by any of the above methods (with the effect of reducing the CNS effects of the compound to an acceptable level), and which exhibits the ability to suppress an immune response, is referred to herein as "a buspirone derivative without significant neuroleptic effect." The efficacy of any such buspirone entity as an immunosuppressant can be tested in the assay described in Example 1 below. Whether the same entity is capable of inducing the neuropharmacological side effects observed for buspirone can be assayed by, for example, the hot plate test of Eddy et al., *J. Pharmacol.* 107:385 (1953) and 110:135 (1954), or by the method of Example 3.

The central nervous system side effects of a buspirone derivative can be estimated using molecular modeling and/or pharmacophore analysis. The dopamine and serotonin receptors are well characterized and strategies for estimating binding of drugs to these receptors are well established. For example, Schmidt, et al., *Molecular Pharmacology* 38:511–516 (1990), describe an algorithm for estimating the binding affinity of drugs to the 5-HT receptor. Also, a composite pharmacophore analysis and chemical database screening strategy is described by Sleight, et al, *Naunyn-Schmiedebergs Arch. Pharmacol.* 343:109–116 (1991), and Schmidt, A. W. and Peroutka, S. J., *Mol. Pharmacol.* 36(4):505–511 (1989).

D. Administration as a Quaternary Salt

Buspirone or its above-defined derivative can be administered in the form of a nontoxic pharmaceutically acceptable quaternary salt. Quaternary salts are typically less lipophilic than the corresponding unquaternized compound, and therefore have a decreased effect on the central nervous system. Nonlimiting examples of quaternary salts that may be used include salts prepared from methyl chloride, methyl bromide, methyl iodide, methyl sulfate, ethyl sulfate, methyl benzene-sulfonate, methyl p-toluenesulfonate, ethyl p-toluenesulfonate, ethyl chloride, ethyl bromide, ethyl iodide, n-propyl chloride, n-propyl bromide, n-butyl bromide, isobutyl bromide, sec-butyl bromide, n-amyl bromide, n-hexyl chloride, benzyl chloride, and benzyl bromide. Other nonlimiting examples of quaternary salts specifically include the quaternary ammonium salt of the formula $—NR^+Z^-$, wherein R is alkyl (and in particular methyl or ethyl) or benzyl, and Z is a counteraniono including chloride, bromide, iodide, —O—alkyl, toluenesulfonate, methylsulfonate, sulfonate, sulfate, phosphate, or carboxylate (such as benzoate, succinate, acetate, glycolate, propionate, maleate, malate, citrate, tartrate, ascorbate, benzoate, cinnamoate, mandeloate, benzyloate, and diphenylacetate).

III. Therapeutic Compositions

Mammals, and specifically humans, suffering from pathogenic immune responses can be treated by administering to the patient an effective amount of the buspirone derivative or its salt in the presence of a pharmaceutically acceptable carrier or diluent.

The buspirone derivative is administered subcutaneously, intravenously, intraperitoneally, intramuscularly, parenterally, orally, submucosally, by inhalation, transdermally via a slow release patch, or topically, in an effective dosage range to cause immunosuppression. Typical systemic dosages for all of the above-identified conditions are those ranging from 2 mg/kg to 0.0001 mg/kg per day as a single daily dose or divided daily doses. Typical dosages for topical application for all of the above-identified conditions are those ranging from 0.001 to 100% by weight of the active compound. In general, local immunosuppression can be achieved by administering topically lower doses of buspirone derivatives than would be required if the agents were administered systemically. The effective dosage of the parent compound, buspirone, for systemic immunosuppression is believed to be higher than the effective dosage of buspirone for inducing a neuroleptic effect.

The buspirone derivative is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound of the buspirone derivative in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. [The active ingredient may be administered once, or may be divided into a number of smaller doses to be administered at varying intervals of time.]

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The buspirone derivative or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The buspirone derivative can also be mixed with other active materials which do not impair the desired action, or with materials that supplement the desired action, such as antibiotics, antifungals, antiinflammatories, antivirals, or other immunosuppressive agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are bacteriostatic water, physiological saline, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein-by reference in its entirety). For example, liposome formulations may be prepared by dissolving appropriate lipid(s)(such as stearoyl phosphatidyl ethanolamine, stearoyl phosphatidyl choline, arachadoyl phosphatidyl choline, and cholesterol) in an organic solvent that is then evaporated, leaving behind a thin film of dried lipid on the surface of the container. An aqueous solution of the buspirone derivative is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene. A number of solutions and ointments are commercially available, especially for ophthalmic applications.

Buspirone derivatives can be provided in the form of pharmaceutically-acceptable salts. As used herein, the term "pharmaceutically-acceptable salts or complexes" refers to salts or complexes that retain the desired biological activity of the parent compound and exhibit minimal, if any, undesired toxicological effects. Examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, and the like, or with an organic cation formed from N,N-dibenzylethylene-diamine or ethylenediamine; or (c) combinations of (a) and (b); e.g., a zinc tannate salt or the like.

Compounds that are useful are those that have a therapeutic index of at least 2, wherein therapeutic index is defined as $EC_{50}/IC_{50}$.

IV. Immunosuppressant Activity of Buspirone Derivatives

Buspirone derivatives are capable of acting systemically or topically to suppress the immune response in animals. As such, the compounds, or therapeutic compositions thereof, may be useful for the treatment of a myriad of immunological disorders.

The ability of the neuroleptic agent buspirone (8-[4-[4-(2-pyrimidinyl)-1-piperaziny]butyl]-8-azaspiro[4.5]decane-7,9-dione) to influence the tissue swelling associated with contact hypersensitivity reactions in mice was evaluated as described in detail in Example 1. The parent buspirone compound was used for the procedure in Example 1 as a model of an active immunosuppressant. Other compounds with a buspirone nucleus can be measured against this model, and are considered active if they suppress the swelling response by at least 40% 24 hours after specific antigen challenge.

When applied topically, preparations of buspirone significantly suppressed the tissue swelling associated with the elicitation phase of contact hypersensitivity to oxazolone. However, mice treated topically with buspirone, unlike those treated systemically, exhibited no drowsiness or other evidence of central nervous system effects.

Buspirone expresses both serotonin and dopamine receptor antagonist activity. However, unlike buspirone, it was discovered that the chemically unrelated serotonin antagonists, trazadone and mianserin, and the dopamine receptor antagonist, haloperidol, were not effective in suppressing contact hypersensitivity. On the basis of this, it appears that the mechanism of action of buspirone on the immune response is independent of its serotonin or dopamine receptor blocking properties, and therefore, buspirone derivatives with immunosuppressive effect yet without neuroleptic effect can be provided by the method of selection disclosed generally herein.

EXAMPLE 1

Inhibition of Induced Contact Hypersensitivity

Six-to-8-week-old female $C_{57}BL/6J$ or BALB/c mice were obtained from the Jackson Laboratory, Bar Harbor, Maine or from Charles River Laboratories, Kingston Facility, Stoneridge, N.Y., respectively.

Buspirone, mianserin, trazadone, haloperidol and oxazolone were purchased from the Sigma Chemical Co. (St. Louis, Mo.).

Oxazolone-Induced Contact Hypersensitivity

Sensitization and challenge for contact hypersensitivity were performed as follows. The abdomens of the mice were shaved with electric clippers, 50 µl of a 4% (w/w) solution of oxazolone in 4:1 (v:v) acetone:olive oil were applied to the shaved abdomen, and 5 µl of the same solution were applied to each hind footpad. Five to eight days later, the mice were challenged for contact hypersensitivity by applying 10 µl of a 0.5% (w:w) solution of oxazolone in 4:1 (v:v) acetone:olive oil to both the inner and outer surface of the right ear of each mouse (in the case of mice treated systemically with buspirone) or to both ears (in the case of mice treated topically with buspirone).

Systemic Buspirone Treatment

One hour after the application of oxazolone for elicitation of contact hypersensitivity, mice were treated subcutaneously with buspirone 500 or 50 mg/kg body weight) in 0.1 ml of carrier (Cremophor EL, BASF, Parsippany, N.J.), or with 0.1 ml of carrier alone. In a separate experiment, mice were treated in a similar fashion with 50 mg/kg body weight of trazadone, mianserin, haloperidol, or buspirone in 1 ml olive oil or with olive oil alone.

Topical Buspirone Treatment

For these experiments, both ears of each mouse were challenged for elicitation of contact hypersensitivity by the application of oxazolone (as appropriate) to both surfaces of both ears. Two hours before, or twenty-four hours after application of hapten, the right ears of some mice were treated with buspirone in vehicle, applied epicutaneously to both surfaces. The right ears of control mice were similarly treated, but with vehicle alone. In the case of experiments designed to evaluate the topical effect on the sensitization phase, only the right ear was challenged (see FIGS. 9 and 10).

Evaluation of Ear Swelling Response

Immediately before and 24 or 48 hours after application of oxazolone, ear thicknesses were determined with an engineer's micrometer. The increment (delta) in ear thickness (ear swelling) was calculated as the 24- or 48-hour value minus the baseline (pre-challenge) value and expressed in units of 104 inches. Mice were killed by cervical dislocation after the measurement of 24-hour ear thickness was obtained, and the ears were processed for histologic examination.

Quantification of Leukocyte Infiltration

Both ears of each mouse were fixed in 4.0% buffered formalin and then processed routinely and embedded in paraffin for preparation of 6-7 µm-thick hematoxylin and eosin-stained sections. All of the sections were coded and examined with an ocular grid at 400× under light microscopy by an observer unaware of the identity of the individual slides. The number of leukocytes/mm$^2$ of dermis was calculated by counting all of the leukocyte cells in an area of at least 0.14 mm$^2$ of dermis.

Statistical Analysis

Differences between groups were assessed by the 2-tailed Student's t test (paired for comparisons of left and right ears in the same mice, unpaired for comparisons between different groups of mice).

Figure 2:
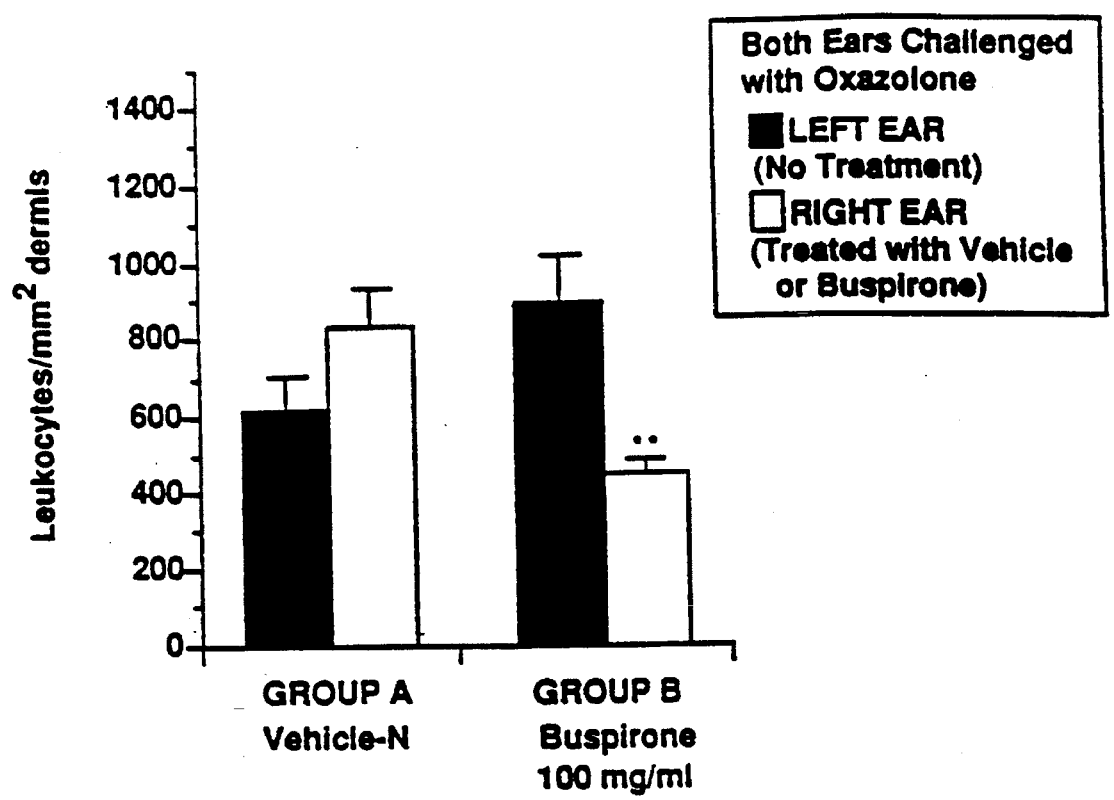
FIGS. 2 and 2a show comparative effects of systemic treatment (subcutaneous administration at 50 mg/kg) with mianserin HCl (Group A), trazadone HCl (Group B), haloperidol (Group C), buspirone HCl (Group D), and systemic vehicle (Group E) on leukocyte infiltration associated with 24-hour contact hypersensitivity reactions. These data (mean±SEM) are derived from the same mice whose ear thickness values are shown in FIG. 3. The reduction in leukocyte infiltration observed in the right (oxazolone-challenged) ears of animals treated with buspirone was significant when compared to the reactions observed in animals treated with vehicle alone (*=p<0.05), while haloperidol, trazadone and mianserin did not significantly suppress the leukocyte infiltration associated with contact hypersensitivity.
Figure 2A:
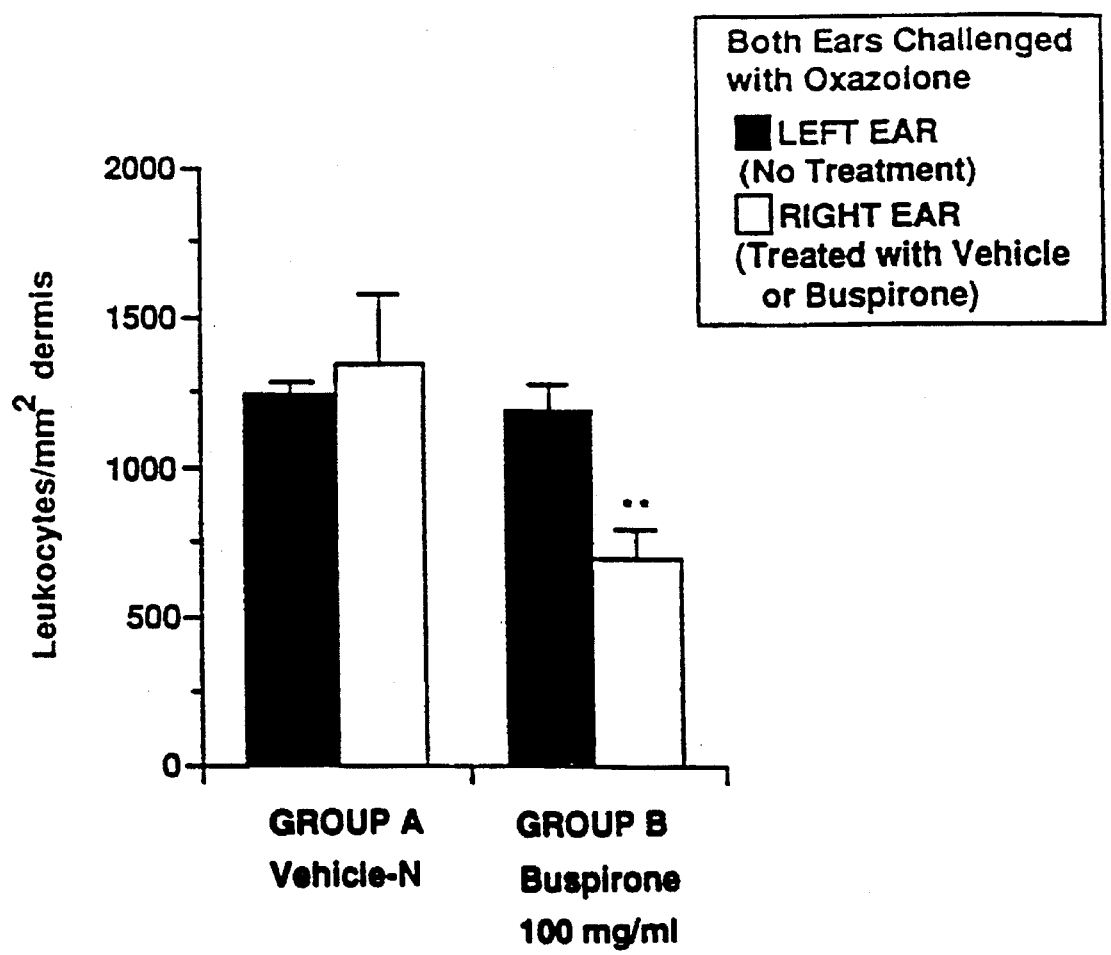

Effect of Systemic Buspirone Versus Other Serotonin or Dopamine Receptor Antagonists In these experiments, systemic buspirone was compared to the serotonin receptor antagonists, trazadone or mianserin, and to the dopamine receptor antagonist, haloperidol, for their ability to inhibit cutaneous contact hypersensitivity. At a dose of 50 mg/kg, only buspirone significantly reduced cutaneous contact hypersensitivity (FIGS. 1, 2).

Effect of Systemic Treatment with Buspirone on Expression of Contact Hypersensitivity The subcutaneous administration of buspirone at dosages of 500 or 50 mg/kg, 1 hour after challenge markedly diminished the tissue swelling which developed in association with the contact hypersensitivity response (FIG. 7). The leukocyte infiltration associated with the response in mice treated with 500 or 50 mg/kg buspirone was also diminished compared to responses in mice not treated with the drug (FIG. 8). However, at these dosages, buspirone also produced other remarkable systemic effects. The mice rapidly became lethargic after administration of the drug, and, by 23 hours after buspirone injection, the mice exhibited profound depression of central nervous system function (these effects were more pronounced at the higher dosage). They appeared to be in a deep sleep, neither ate nor drank, and responded weakly or not at all to touch. They did, however, exhibit responsiveness to pinch in both doses.

EXAMPLE 2

Comparison of Immunosuppressant Versus Anti-Inflammatory Activity

Mice were sensitized to oxazolone as described in Example 1. Three days later, slow release indomethacin pellets (0.05 mg, 3 week release) were implanted subcutaneously under light ether anesthesia. The dose of indomethacin delivered by these pellets has been previously shown to completely block prostaglandin synthesis in mice, by Jun, D. D., et al., *J. Invest. Dermatol.* 90:311 (1988).

Three days later, mice were challenged for contact hypersensitivity as in Example 1. When the hypersensitivity response was assessed 24 hours later, indomethacin was shown to have no significant effect on the response. A classic anti-inflammatory agent, indomethacin, does not appear to suppress the edema associated with the immunologically specific oxazolone induced contact hypersensitivity response, and, compared to buspirone, only weakly suppress the leukocyte infiltration associated with the response.

EXAMPLE 3

Evaluation of Serotonin Receptor Binding Activity or Dopamine Receptor Binding Activity of Buspirone Derivatives Buspirone derivatives which lack serotonin receptor binding or dopamine receptor binding activity can be identified as follows. A radiolabeled ligand known to bind serotonin and/or dopamine receptors can be bound to an appropriate substrate expressing one or both of these receptors. For example, radiolabeled quipazine which is available commercially can be used as the ligand. The buspirone derivative to be tested is then incubated with the radiolabeled quipazine ligand combination. Displacement of radiolabeled ligand is positive evidence that the buspirone derivative being tested can bind serotonin and/or dopamine receptors. The amount of radiolabeled ligand which is displaced is determined by an appropriate standard curve which can also provide information concerning binding affinities. The displaced radiolabeled ligand can be quantitated using a standard scintillation counter.

A detailed description of how to perform the binding studies using $^3$H-quipazine and the example follows:

Binding studies using $^3$H-quipazine are described in detail by Milburn, C. M. and Peroutka, S. J., *J. Neurochem.* 52:1787–1792 (1989). Briefly, rat cortices are homogenized in 20 volumes of 50 mM Tris HCl buffer pH 7.7 at 25° C. and centrifuged at 49,000×g for 10 min. The pellet is resuspended in fresh buffer and incubated at 37° C. for 10 min. After the final centrifugation, the pellet is resuspended in 80 volumes of Krebs-HEPES buffer (25 mM HEPES, 118 mM NaCl, 5 mM KCl, 2.5 mM $CaCl_2$, and 1.2 mM $MgCl_2$ pH adjusted to 7.4). Tissue (10 mg of original wet weight) is added to assay tubes containing 0.8 nM [$^3$H]quipazine and displacing drug or buffer in a final volume of 1 ml. Non-specific binding is defined using 1 micromole zacopride. After a 30 min incubation at room temperature, the tissue is rapidly filtered under vacuum through No. 32 glass fiber filters and rinsed twice with 5 ml of 50 mM Tris-HCl buffer pH 7.7. Radioactivity is quantified by liquid scintillation counting. All experiments are performed three to six times, each in triplicate. This same approach can be used with other radiolabeled ligands such as zacopride, granisetron, haloperidol, mianserin, ketanserin, 5-HT, dopamine, droperidol, or ritanserin.

Buspirone derivatives that have binding affinities for dopamine and/or serotonin receptors of one/tenth or less than parent buspirone are considered to be potentially useful as systemic immunosuppressants if they are at least 50% as active as parent buspirone on a weight basis in suppressing immunologically specific responses such as contact hypersensitivity.

Modifications and variations of the present invention relating to methods for the treatment of pathology associated with immune responses that includes topical administration of an effective amount of buspirone or a buspirone derivative will be obvious to those skilled in the art from the foregoing detailed description of the invention. Such modifications and variations are intended to come within the scope of the appended claims.

We claim:

1. A method for treating a mammal in need of immunosuppression, comprising systemicaly administering to the mammal an effective amount of buspirone or its pharmaceutically acceptable salt, other than a quaternary salt, in a pharmaceutically-acceptable diluent or carrier.

2. The method of claim 1 wherein the mammal is a human.

3. The method of claim 1, wherein the mammal is a human in need of immunosuppression due to contact hypersensitivity.

4. The method of claim 1, wherein the buspirone has a therapeutic index of at least 2.

5. The method of claim 1, wherein buspirone or its pharmaceutically acceptable salt is administered orally.

6. The method of claim 1, wherein buspirone or its pharmaceutically acceptable salt is administered parenterally.

7. The method of claim 1, wherein buspirone, or its pharmaceutically acceptable salt, is administered intravenously.

8. The method of claim 1, wherein the dosage is between 2.5 mg/kg and 0.001 mg/kg of body weight per day as a single daily dose or divided daily doses.

9. The method of claim 1, wherein buspirone or its pharmaceutically acceptable salt is administered in a time release formulation.

10. The method of claim 1, wherein buspirone is administered as a pharmaceutically acceptable salt.

* * * * *